(12) United States Patent
Aalders et al.

(10) Patent No.: US 9,278,167 B2
(45) Date of Patent: Mar. 8, 2016

(54) ACTUATOR CONTROL IN A BREAST PUMP SYSTEM

(71) Applicant: KONINKLIJKE PHILIPS N.V., Eindhoven (NL)

(72) Inventors: Arnold Aalders, Eindhoven (NL); Michiel Dirk Augustinus Bijloo, Eindhoven (NL); Alexander Cornelis Geerlings, Eindhoven (NL); Godefridus Gertruda Willem Beulen, Eindhoven (NL); Theodorus Johannes Adrianus Maria Den Bekker, Eindhoven (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 0 days.

(21) Appl. No.: 14/429,931

(22) PCT Filed: Aug. 13, 2013

(86) PCT No.: PCT/EP2013/066900
§ 371 (c)(1),
(2) Date: Mar. 20, 2015

(87) PCT Pub. No.: WO2014/044472
PCT Pub. Date: Mar. 27, 2014

(65) Prior Publication Data
US 2015/0209497 A1   Jul. 30, 2015

Related U.S. Application Data

(60) Provisional application No. 61/704,676, filed on Sep. 24, 2012.

(30) Foreign Application Priority Data

Sep. 24, 2012 (EP) .................................. 12185595

(51) Int. Cl.
A61M 31/00 (2006.01)
A61M 1/06 (2006.01)
A61M 1/00 (2006.01)

(52) U.S. Cl.
CPC ............. *A61M 1/064* (2014.02); *A61M 1/0031* (2013.01); *A61M 1/0037* (2013.01); *A61M 1/06* (2013.01)

(58) Field of Classification Search
CPC .... A61M 1/0037; A61M 1/06; A61M 1/0035
See application file for complete search history.

(56) References Cited

U.S. PATENT DOCUMENTS

| 6,547,756 | B1 | 4/2003 | Greter |
| 2007/0135761 | A1 | 6/2007 | Cheng |
| 2008/0009815 | A1 | 1/2008 | Grabenkort |
| 2008/0177224 | A1 | 7/2008 | Kelly |
| 2011/0004154 | A1 | 1/2011 | Van Schijndel |
| 2011/0270162 | A1 | 11/2011 | Guo |

FOREIGN PATENT DOCUMENTS

EP   1586340 A2   10/2005

*Primary Examiner* — Kevin C Sirmons
*Assistant Examiner* — Deanna K Hall

(57) ABSTRACT

The present application relates to a breast pump system comprising a pump unit, an actuator for driving the pump unit, and a power supply for supplying electrical power to the actuator, and also to a method for use in such as system. An actuator speed regulating module is provided to drive the actuator at a first speed when the pump unit is turned on, and to continue to drive the actuator at a second speed higher than the first speed after a load on the actuator reaches a predetermined level.

15 Claims, 7 Drawing Sheets

ACTUATOR CONTROL IN A BREAST PUMP SYSTEM

This application is the U.S. National Phase application under 35 U.S.C. §371 of International Application No. PCT/EP2013/066900, filed on Aug. 13, 2013, which claims the benefit of U.S. Provisional Application No. 61/704,676 filed on Sep. 24, 2012 and European Application No. 12185595.1 filed Sep. 24, 2012. These applications are hereby incorporated by reference herein.

FIELD OF THE INVENTION

The present application relates to breast pumps. More particularly, the present application relates to actuator control in a breast pump system, in which an actuator is initially supplied with a low voltage when turned on and supplied with a higher voltage after a predetermined time period.

BACKGROUND OF THE INVENTION

Breast pumps are used by mothers to express breast milk at a convenient time, to be stored for later consumption by their child. The breast pump operates by generating a vacuum to mimic the feeding action of the child. Conventional breast pumps can be categorised as mechanical, in which a user manually operates a vacuum pump in order to generate the required vacuum, or electrical, in which a vacuum pump is driven by an electric motor. In electrical breast pumps, it is generally desirable to reduce a power consumption of the system, improve reliability of the system to avoid potential injury to a user, and reduce noise levels associated with the operation of the breast pump. High noise levels can prevent a mother from being able to relax and so the let-down reflex needed to ensure milk expression may be affected.

The invention is made in this context.

US 2008/009815 A1 discloses a closed-loop vacuum control system for a powered breast pump. The vacuum control system includes a source of vacuum for applying a vacuum to a milk collection kit. It also includes a device for setting the vacuum level to be produced by the source of vacuum to a preselected vacuum level. The vacuum control system further includes a sensor for sensing the actual vacuum level being produced by the source of vacuum during operation. A controller continuously compares the preselected vacuum level with the actual vacuum level. A proportional valve is also provided for adjusting the actual vacuum level to correspond to the preselected vacuum level. In this manner, the proportional valve can adjust the actual vacuum level in response to a signal from the controller.

SUMMARY OF THE INVENTION

It is an object of the invention to provide a breast pump system and method which substantially alleviates or overcomes one or more of the problems mentioned above.

According to the present invention, there is provided a breast pump system comprising a pump unit, an actuator for driving the pump unit, a power supply arranged to supply electrical power to the actuator, and an actuator speed regulating module arranged to drive the electric motor at a first speed when the vacuum pump is turned on, and to continue to drive the electric motor at a second speed higher than the first speed after a load on the motor reaches a predetermined level. This can avoid the motor running at a high speed and generating excessive noise, when the motor is initially turned on and the load is low.

The actuator may be an electric motor, such as a direct current DC electric motor.

The power supply may be arranged to supply the electrical power to the actuator using pulse width modulation PWM, and may be arranged to supply the first voltage by supplying the electrical power with a first duty cycle and to supply the second voltage by supplying the electrical power with a second duty cycle higher than the first duty cycle. This allows the actuator control to be applied to existing PWM designs without the need for additional hardware.

The power supply may be arranged to gradually increase the first voltage up to the second voltage during the predetermined time period. The actuator resistance gradually increases as the speed of rotation increases, and ramping the first voltage up to the second voltage during the time period can provide smooth acceleration of the actuator during the time period.

The breast pump system may further comprise a power supply control module arranged to detect an input current supplied to the actuator and reduce the speed of the actuator in response to the detected input current exceeding a threshold current level indicative of a threshold vacuum level at a breast pump. This can avoid the pump continuing to run in situations where there is already a high vacuum at the breast pump and further use of the pump could increase the vacuum further.

The power supply control module may be arranged to suspend the supply of electrical power to the actuator in order to reduce the speed of the actuator. In this way the pump unit can be turned off as soon as the threshold current is exceeded, preventing the vacuum from increasing any further.

The pump unit may further comprise a vacuum pump and a valve for releasing a vacuum generated by the vacuum pump, wherein in response to the detected input current exceeding the threshold current level, the power supply control module may be further arranged to indicate a failure of the valve. This has the advantage that a failure of the valve can be detected, allowing appropriate action to be taken, for example by notifying a user that the valve should be repaired or replaced.

The power supply may be arranged to supply the electrical power to the actuator using pulse width modulation PWM according to a duty cycle, and the power supply control module is arranged to suspend the supply of electrical power to the actuator by setting the PWM duty cycle to substantially zero. This approach allows the actuator cut-off function to be performed by a PWM controller, and so additional hardware to isolate the actuator is not required.

The breast pump system may further comprise an actuator speed regulating module arranged to drive the actuator at a first speed when the pump unit is turned on, and to continue to drive the actuator at a second speed higher than the first speed after a load on the actuator reaches a predetermined level. This can avoid the actuator running at a high speed and generating excessive noise, when the actuator is initially turned on and the load is low.

The second predetermined time period may be a time taken for a pressure difference generated by the pump unit to reach a predetermined level. The predetermined level can be chosen as a level at which the back-pressure of working against the pressure difference is able to regulate the pump speed to maintain noise within acceptable levels.

The breast pump system may further comprise a breast pump having a chamber, and a membrane receivable in the chamber to separate the chamber into first and second spaces, wherein the membrane is deformable in the chamber in response to a reduction of pressure in the first space to cause a reduction of pressure in the second space, and a surface of the chamber contactable with the membrane, and/or a surface of the membrane contactable with the chamber, may have a textured surface finish so that the noise level generated as the membrane comes into contact with, moves along, or moves away from, the chamber is minimised. This acts to reduce the noise level generated by a surface of the flexible membrane coming into contact with, moving along, or moving away from, a surface of the chamber. The textured surface finish acts to reduce the surface area of the membrane and chamber in contact with each other.

In one embodiment, the surface of the chamber contactable with the membrane may have a textured surface finish. With this arrangement the textured surface is easily formed due to the rigidity of the shell forming the chamber.

In another embodiment, the surface of the membrane contactable with the chamber may have a textured surface finish.

The chamber may comprise a sidewall against which the membrane locates prior to and/or during deformation wherein the surface having the textured surface finish may be formed by the sidewall and/or the section of membrane contactable with the sidewall. Therefore, the surface area of the surface of the membrane in contact with the circumferential surface of the sidewall extending around the membrane, against which the membrane is urged, is minimised.

The surface may have a textured surface finish with an arithmetical mean roughness (Ra) of about Ra 1.6 µm.

The surface may have a textured surface finish with an arithmetical mean roughness (Ra) greater than Ra 0.8 µm. One advantage of the above arrangement is that having a textured surface finish of greater than Ra 0.8 µm reduces the noise generated by the surface of the membrane moving over the surface of the chamber.

The surface may have a textured surface finish with an arithmetical mean roughness (Ra) of less than Ra 3.2 µm. One advantage of the above arrangement is that having a textured surface finish of less than Ra 3.2 µm restricts excessive wear of the membrane as it moves over the surface of the chamber.

In yet another embodiment, the surface of the chamber contactable with membrane and the surface of the membrane contactable with the chamber may both have a textured surface finish.

In such an embodiment, the surfaces of the chamber and the surface of the membrane may each have a textured surface finish with an arithmetical mean roughness (Ra) greater than Ra 0.4 µm. One advantage of the above arrangement is that each surface having a textured surface finish minimises the arithmetical mean roughness (Ra) required to minimise the noise generated by the surface of the membrane moving over, into contact or away from the surface of the chamber.

According to another aspect of the present invention, there is also provided a breast pump comprising a chamber, and a membrane receivable in the chamber to separate the chamber into first and second spaces, wherein the membrane is deformable in the chamber in response to a reduction of pressure in the first space to cause a reduction of pressure in the second space, and a surface of the chamber contactable with the membrane, and/or a surface of the membrane contactable with the chamber, has a textured surface finish so that the noise level generated as the membrane comes into contact with, or moves away from, the chamber is minimised.

According to the present invention, there is also provided a method for use in a breast pump system comprising a vacuum pump, a direct current DC electric motor for driving the vacuum pump, and a power supply arranged to supply electrical power to the electric motor, the method comprising driving the electric motor at a first speed when the vacuum pump is turned on, and continuing to drive the electric motor at a second speed higher than the first speed after the second predetermined time period after the motor is turned on.

The method can further comprise detecting an input current supplied to the electric motor, and reducing the speed of the electric motor in response to the detected input current exceeding a threshold current level indicative of a threshold vacuum level at a breast pump.

The method can further comprise supplying the electrical power by supplying a first voltage to the electric motor when the vacuum pump is turned on, and supplying a second voltage, higher than the first voltage, to the electric motor after a predetermined time period after the motor is turned on.

According to the present invention, there is further provided a breast pump system comprising a vacuum pump, a direct current DC electric motor for driving the vacuum pump, a power supply arranged to supply electrical power to the electric motor, and a power supply control module arranged to detect an input current supplied to the electric motor and reduce the speed of the electric motor in response to the detected input current exceeding a threshold current level indicative of a threshold vacuum level at a breast pump. This can avoid the pump continuing to run in situations where there is already a high vacuum at the breast pump and further use of the pump could increase the vacuum to a level that could cause discomfort or injury to a user.

According to the present invention, there is further provided a breast pump system comprising a vacuum pump, a direct current DC electric motor for driving the vacuum pump, a power supply arranged to supply electrical power to the electric motor, and a power supply control module arranged to control the power supply to supply a first voltage to the actuator when the pump unit is turned on and to supply a second voltage, higher than the first voltage, to the actuator after a predetermined time period after the actuator is turned on. By starting the actuator using a lower voltage, a high inrush current can be avoided and the actuator power consumption can be reduced.

These and other aspects of the invention will be apparent from and elucidated with reference to the embodiments described hereinafter.

BRIEF DESCRIPTION OF THE DRAWINGS

Embodiments of the invention will now be described, by way of example only, with reference to the accompanying drawings, in which.

DETAILED DESCRIPTION OF THE EMBODIMENTS

Figure 1:
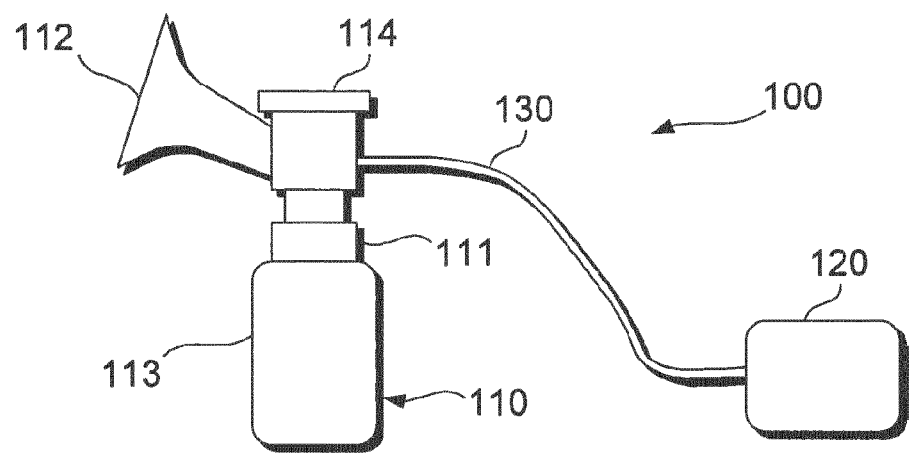
FIG. 1 illustrates a breast pump system.
Figure 2:
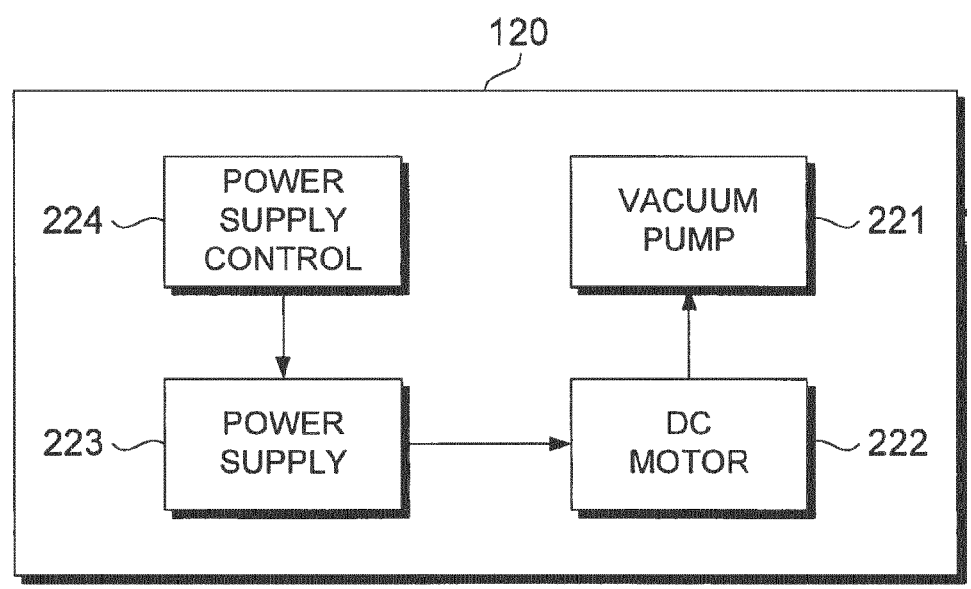
FIG. 2 illustrates the operating unit of the breast pump system of FIG. 1.

Referring now to FIGS. 1 and 2, a breast pump system is illustrated. As shown in FIG. 1, the breast pump system 100 includes a breast pump 110, also known as an expression unit, and an operating unit 120 connected by a tube 130 to the breast pump 110. The tube 130 provides a fluid communication between the breast pump 110 and the operating unit 120. The tube 130 may also be used to provide an electrical connection between the breast pump 110 and the operating unit 120. For example, the tube may supply an operating signal or electrical power between the breast pump and the operating unit. Although the operating unit 130 is spaced from the breast pump 110 in the present arrangement, it will be understood that the operating unit may be integrally formed with the breast pump 110.

The breast pump 110 has a main body 111, funnel 112, collection vessel 113 and a diaphragm 114 coupled to the vacuum line 130. The collection vessel 113, or receptacle, collects milk expressed from a user's breast and may take the form of a feeding bottle or bag. The collection vessel 113 is attached to the main body 111 by a screw fitting, although it will be understood that alternative releasable attachment means may be used, such as clips (not shown). The breast-receiving funnel 112 is configured to receive the breast of a user, and has a mouth and a throat. The mouth is open at an outer end of the funnel 112, and the funnel 112 converges from the outer end towards the throat to form a hollow recess in which a breast is received. The main body 111 fluidly connects the funnel 112 to the collection vessel 113. A fluid passageway is formed through the main body 111 from the breast receiving space of the funnel 112 to the collection vessel 113. The main body 111 is formed from an outer shell. The main body 111 is integrally formed with the funnel 112, however it will be understood that the funnel 112 may be detachable.

The operating unit 120 comprises a pump unit and an electric motor for driving the pump unit (not shown in FIG. 1). The electric motor acts as an actuator. The pump unit is configured to generate and release a pressure reduction in a vacuum path. The means for generating the pressure reduction and the means for releasing the pressure reduction are separate components. In particular, in the present embodiment the vacuum unit comprises a vacuum pump (not shown in FIG. 1) and a pressure release valve (not shown in FIG. 1). The vacuum pump acts as a pressure reduction means. The pressure release valve acts as a means for releasing a pressure reduction. The vacuum pump is fluidly connected to the main body 111 via the tube 130. The release valve is configured to cyclically open to release the reduction in pressure generated by the vacuum pump. This causes a cyclical pressure differential to be generated. However it will be understood that a different vacuum generating system could also be used. For example, it will be understood that the means for generating the pressure reduction and the means for releasing the pressure reduction may be integrally formed.

A chamber is formed in the main body 111 of the breast pump 110. The chamber is formed along the fluid passageway, and has a vacuum port. The vacuum port communicates with the tube 130 so that the vacuum pump is able to cause a pressure reduction in the chamber.

In the present embodiment, a membrane is received in the chamber. The membrane, also known as a diaphragm, is flexible. The membrane separates the chamber into a first space and a second space. The first space is in fluid communication with the vacuum port. Therefore, a pressure reduction is generated in the first space by the vacuum pump. The second space is in fluid communication with the fluid passageway between the breast receiving space of the funnel 112 and the collection vessel 113. Therefore, the second space is in direct fluid communication with a breast received in the funnel. A one-way valve is disposed between the chamber and the collection vessel 113. When a pressure reduction is generated in the first space, the membrane deforms and is drawn in the direction of the first space. Therefore, a pressure reduction is produced in the second space of the chamber due to the deformation of the membrane. When a breast is received in the mouth of the funnel, a pressure reduction is formed in the funnel which acts on the user's breast and urges milk to be expressed therefrom.

The above arrangement indirectly generates a vacuum at a user's breast. It will be understood that it is also possible to generate a vacuum at a user's breast by omitting the membrane so that a direct fluid connection is formed between the vacuum pump and the funnel. Furthermore, although in the present embodiment separate breast pump and operating units are provided, in other embodiments the breast pump system components such as the collector, funnel, vacuum pump, electric motor and power supply, may be housed in a single body. For example, components of the operating unit may be integrated into the main body of the breast pump, removing the need for a separate operating unit.

The operating unit 120 is illustrated in more detail in FIG. 2, and comprises a vacuum pump 221 for generating a vacuum, a direct-current (DC) electric motor 222 for driving the vacuum pump 221, a power supply 223 for supplying electrical power to the electric motor 222, and a power supply control module 224 for controlling the power supply 223. The power supply control module 224 is arranged to control the power supply 223 to supply a first voltage to the electric motor 222 when the vacuum pump is turned on and to supply a second voltage, higher than the first voltage, to the electric motor 222 after a predetermined time period after the motor 222 is turned on. This can avoid a high inrush current when the motor 222 is initially turned on and the motor resistance is low, as will now be described with reference to FIG. 3.

The present embodiments relate to a breast pump system comprising a DC brushed electric motor. However, it will be understood that the present invention is also applicable to breast pump systems including alternative types of motor. For example, in another arrangement including an alternative type of motor, or a DC brushed electric motor, a voltage drop may be caused by a loose wire or a different fault.

Figure 3:
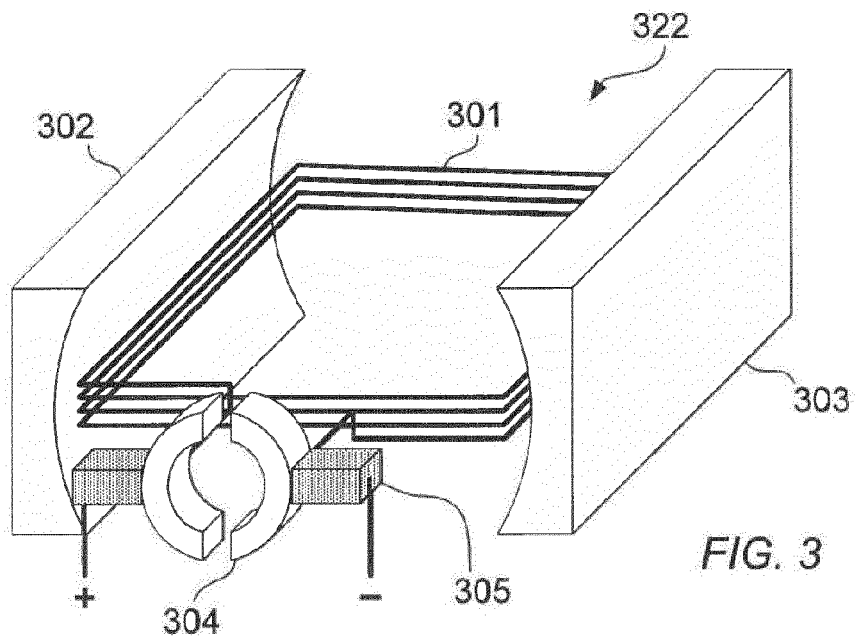
FIG. 3 illustrates a direct-current electric motor for use in a breast pump system.

FIG. 3 illustrates a DC electric motor 322 for use in a breast pump system such as the one shown in FIGS. 1 and 2. The electric motor 322 comprises a coil 301 of wire wrapped around an armature, which is omitted in FIG. 3 for clarity. Permanent magnets 302, 303 are positioned on opposite sides of the coil 301, which is connected to a power supply through commutator segments 304 and carbon brushes 305. As such, the motor 322 can be referred to as a DC brushed electric motor. However, the present invention is not limited to use with DC brushed motors, and in other embodiments other types of DC motor, for example brushless motors, may be used. The skilled person will be familiar with the operating principles of a DC brushed electric motor, and as such a detailed description will be omitted here to maintain brevity. Although two commutator segments 304 are shown in FIG. 3, in general any number of two or more segments may be provided.

As the armature rotates, the current flowing in the coil 301 generates a counter-electromotive force (EMF) field which opposes the rotation of the armature and coil 301. This counter-EMF field results in an increased resistance when the motor 322 is spinning at high speeds. However, when the motor 322 is initially turned on, there is no counter-EMF field and the only resistance is provided by the coil 301 itself, which may be negligible. This can lead to a current spike when the motor is initially turned on. In embodiments of the present invention the power supply is controlled to supply a low voltage when the motor is initially turned on, and increase this to a higher voltage as the motor speed increases and the resistance increases. The supply voltage can be increased after a predetermined time period, which can be a time taken for the motor to reach a desired operating speed. This approach can avoid the initial current spike, which can be referred to as an inrush current, and hence can reduce the overall power consumption of the motor during use. Also, damage associated with the inrush current, for example due to sparking between the commutator segments 304 and brushes 305, can be avoided, reducing wear on the carbon brushes and extending the operating lifetime of the motor 322.

Figure 4:
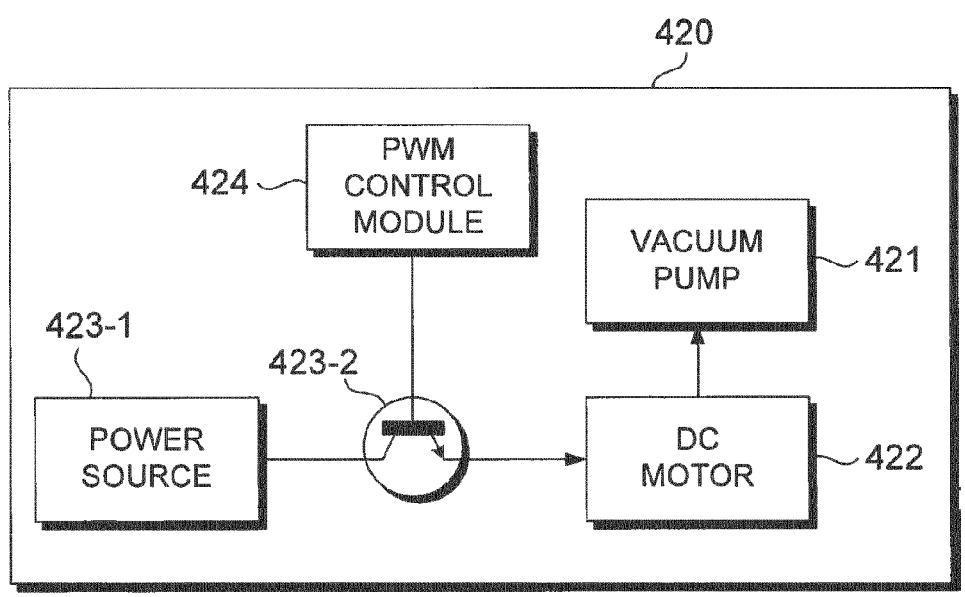
FIG. 4 illustrates a breast pump system using pulse-width modulation control.

Referring now to FIG. 4, a breast pump system using pulse-width modulation control is illustrated, according to an embodiment of the present invention. In the present embodiment an operating unit 420 is provided for use in a breast pump system such as that shown in FIG. 1. The operating unit 420 is similar to the operating unit of FIG. 2, comprising a vacuum pump 421, DC electric motor 422, power supply, and power supply control module 424. It will be appreciated that in other embodiments the components of the operating unit 420 and a collecting unit can be integrated into a breast pump main body, instead of providing physically separate operating and collecting units.

In more detail, in the present embodiment the power supply is arranged to supply power to the electric motor 422 using pulse width modulation (PWM). The power supply includes a power source 423-1 and a field effect transistor (FET) 423-2. In other embodiments however a different type of switch, other than a FET, may be used to switch the power on and off for PWM control. The power supply control module 424 is a PWM control module arranged to control the switch 423-2 used for PWM control. The PWM control module 424 can supply electrical power at a low voltage when the motor is turned on by controlling the PWM switch 423-2 with a first duty cycle, and supply electrical power at a higher voltage after a predetermined time period by increasing the duty cycle. In this way, the control method can be integrated into an existing PWM design without the need for additional hardware.

Furthermore, the flexibility of the PWM control method allows different voltage ramp profiles to be applied when increasing the voltage from the first voltage to the second voltage over the predetermined time period. In one embodiment the voltage can be increase linearly from the first to the second voltage during the predetermined time period. In another embodiment, power can be supplied at the first voltage for the duration of the predetermined time period, and increased directly to the second voltage at the end of the predetermined time period. It will be appreciated that other ramp shapes are also possible, and embodiments of the invention are not limited to these examples.

Figure 5:
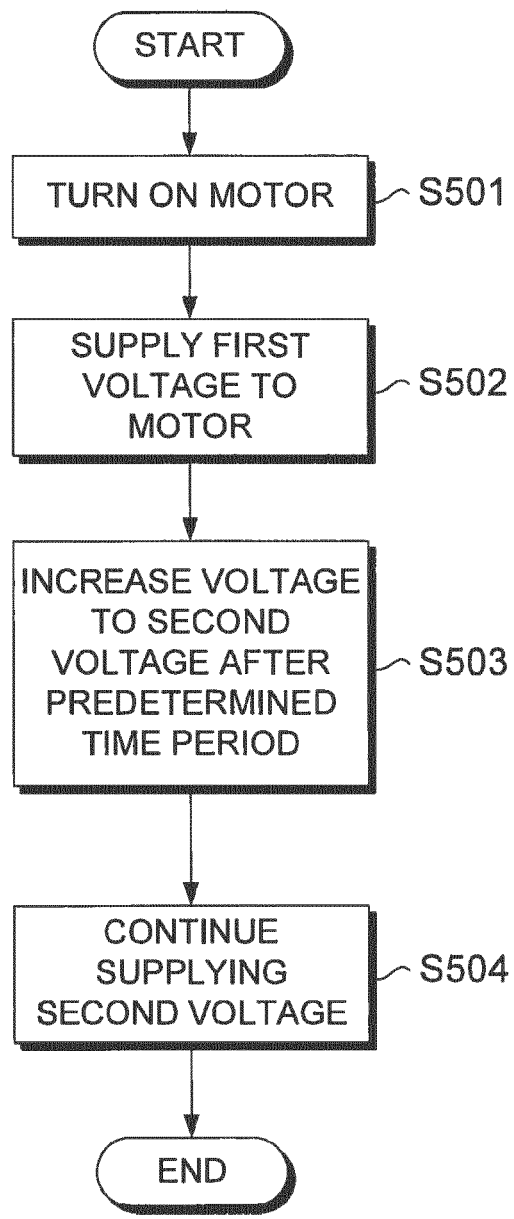
FIG. 5 illustrates a method of supplying power to an electric motor in a breast pump system.

Referring now to FIG. 5, a method of supplying power to an electric motor in a breast pump system is illustrated. The method can be used to control a power supply arranged to supply electrical power to the electric motor. In a first step S501, a signal is received to turn on the electric motor in order to begin driving the vacuum pump. The signal can, for instance, be received from a user, or from control software configured to control operations of the breast pump system. Then, in step S502, the power supply begins to supply power to the motor at a first voltage.

Next, in step S503, the first voltage is increased to the second voltage after the predetermined time period. The predetermined time period can be the time taken for the motor to reach a desired operating speed, at which point the resistance induced by the counter-EMF field is sufficient for the higher second voltage to be applied without resulting in a loss of power due to a current spike. As described above, the voltage can be increased gradually over the duration of the time period to provide smooth acceleration of the motor. Alternatively a step increase can be applied at the end of the time period to increase the voltage directly from the first voltage to the second voltage. A gradual ramp may be readily implemented in a PWM system, whereas in a non-PWM system a step increase may be more easily applied as the power supply only needs to be capable of supplying two discrete voltages, namely the first and second voltages. Finally, in step S504, after the time period has elapsed the power supply continues to supply electrical power to the motor at the second voltage.

Figure 6:
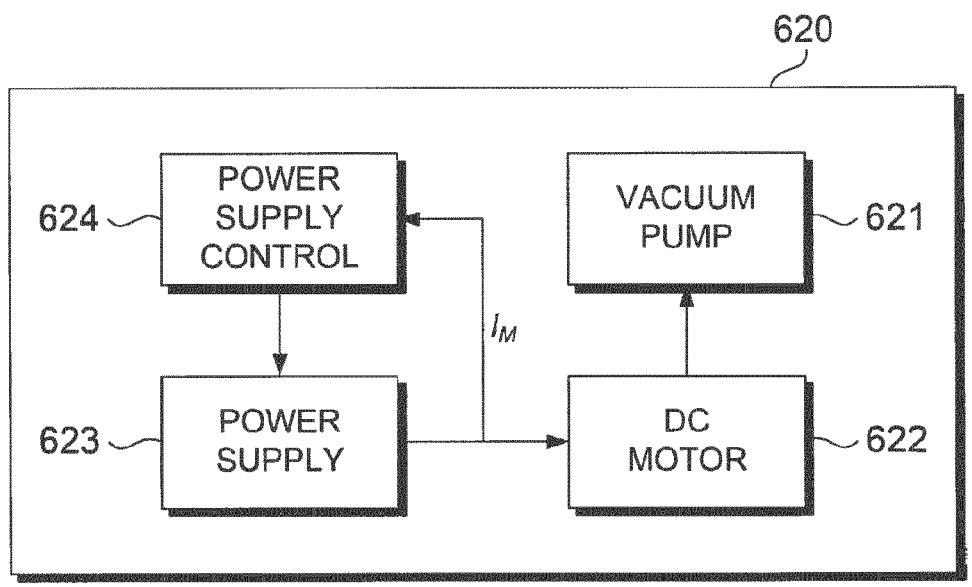
FIG. 6 illustrates a breast pump system.

Referring now to FIG. 6, a breast pump system is illustrated. In the present embodiment an operating unit 620 is provided for use in a breast pump system such as that shown in FIG. 1. The operating unit 620 is similar to the operating unit of FIG. 2, comprising a vacuum pump 621, DC electric motor 622, power supply 623, and power supply control module 624. It will be appreciated that in other embodiments the components of the operating unit 620 and a collecting unit can be integrated into a breast pump main body, instead of providing physically separate operating and collecting units.

In more detail, in the present embodiment the power supply control module 624 is arranged to detect an input current supplied to the motor 622 by the power supply 623, which may be referred to as the motor current $I_M$. The power supply control module 624 can directly detect the motor current, or can receive the result of a current measurement from a separate current detecting module (not shown).

By monitoring the motor current, the power supply control module 624 can determine whether a vacuum condition already exists at the breast pump funnel when the motor 622 is turned on. In normal operation the vacuum should be released after each pumping cycle, by opening a release valve (not shown in FIG. 6). However, if for any other reason the vacuum has not been released, for instance because the release valve has failed to open or an inlet to the valve has become blocked, the initial load on the pump 621 will be higher when the pump 621 is turned on at the start of the next cycle, compared to a situation in which the vacuum has been released after the previous cycle. Specifically, the load when the vacuum has not been released, or has only been partially released, will be higher as the pump 621 is required to work against the pre-existing vacuum condition.

In the present embodiment the level of the motor current at any point is used as an indicator of the vacuum pressure at the present moment in time. A high motor current indicates that the motor 622 is drawing more power as a result of the load on the pump 621 being higher. If the motor current exceeds a predetermined threshold current indicative of a pre-existing vacuum condition, the power supply control is arranged to reduce the speed of the electric motor. In the present embodiment the power supply control is arranged to suspend the supply of electrical power to the motor in order to turn the motor off. In other embodiments however the motor speed can be reduced without the motor being turned off completely.

By reducing the motor speed when the threshold current is exceeded, it is possible for embodiments to avoid an excessively high vacuum developing at the breast pump funnel even when a normal release mechanism has failed. Such embodiments can allow a powerful pump 621 to be used, capable of reaching a desired vacuum level more quickly, without a risk of a high vacuum being developed at the breast pump funnel if the vacuum is not correctly released at the end of each cycle. In other embodiments the current-control process described above can be omitted, for instance if a lower-power pump is used that is not capable of generating a high enough vacuum to cause discomfort or injury to a user.

Figure 7:
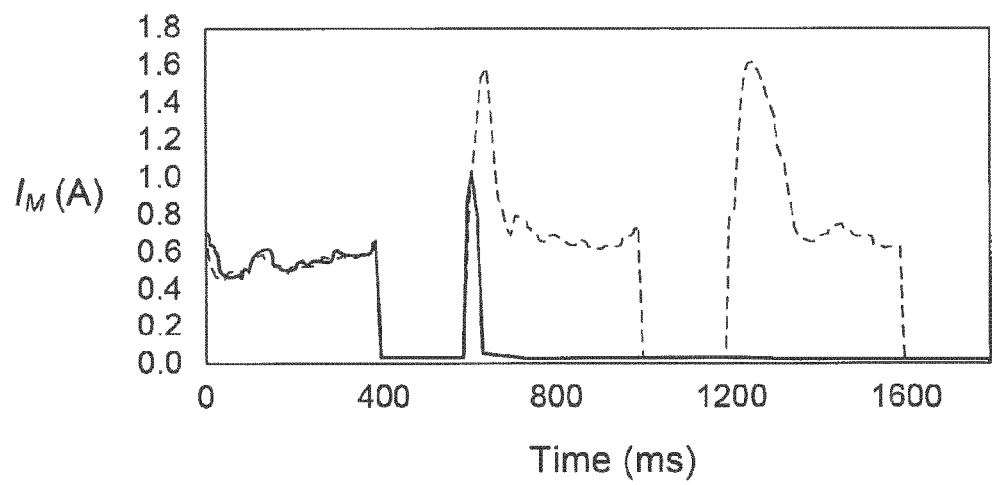
FIG. 7 illustrates a graph showing a motor current profile over time in the breast pump system of FIG. 6.

Referring now to FIG. 7, a graph showing a motor current profile over time in the breast pump system of FIG. 6 is illustrated. The graph plots the motor current $I_M$ against time, over three pumping cycles. A dashed line illustrates the measured motor current level during each pumping cycle when the current control method described above with reference to FIG. 6 is not used. A high current is observed at the start of each pumping cycle as the release valve has failed, and the vacuum from the previous pumping cycle has not been released. In contrast, the solid line in FIG. 7 illustrates the measured motor current level when the current control is applied. Again, after the first pumping cycle the vacuum is not released as the release valve has failed to operate. However, because current control is applied, the pump is stopped as the threshold current is exceeded. By applying the current control method described above with reference to FIG. 6, the system can therefore rapidly detect the existence of a high vacuum level at the breast pump funnel, and reduce the motor speed to prevent the vacuum increasing further.

Figure 8:
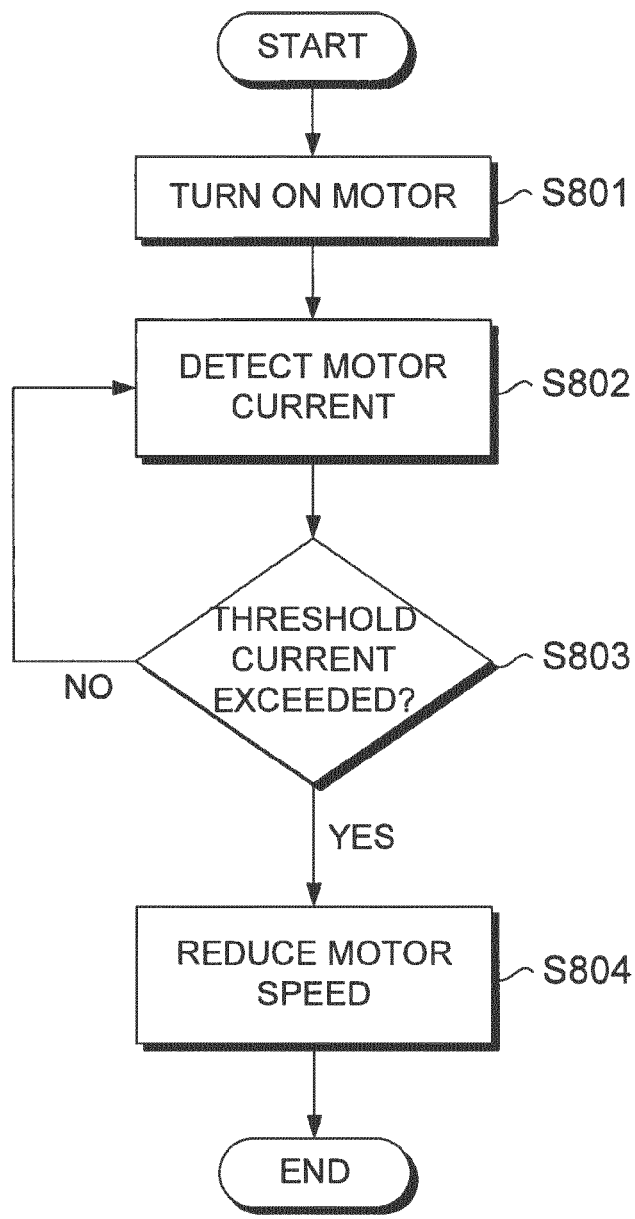
FIG. 8 illustrates a method for use in a breast pump system such as the one shown in FIG. 6.

Referring now to FIG. 8, a method for use in a breast pump system such as the one shown in FIG. 6 is illustrated. In a first step S801, the electric motor is turned on. Then, in step S802, the motor current is detected. Next, in step S803, the detected motor current is compared to the predetermined threshold current, which is indicative of a threshold vacuum level at a breast pump. If the threshold current has not been exceeded, the process returns to step S802 and continues to monitor the motor current. If however the threshold current has been exceeded, then in step S804 the motor speed is reduced. For example, the motor speed can be reduced by decreasing a driving voltage supplied to the motor, or by disconnecting the motor from the power supply. As explained above, a method such as the one shown in FIG. 8 can detect the existence of a high vacuum level at the breast pump funnel, and reduce the motor speed to prevent the vacuum increasing further.

In the embodiments described with reference to FIGS. 6, 7 and 8 the breast pump system is also arranged to control the electric motor as described above with reference to FIG. 5, specifically by supplying power at a lower voltage when the motor is turned on and increasing the power to a higher voltage after a predetermined time period. However, in other embodiments the current control process described in FIGS. 6, 7 and 8 to prevent a high vacuum occurring can be applied to any conventional breast pump system regardless of whether or not the motor control method of FIG. 5 is also used.

Figure 9:
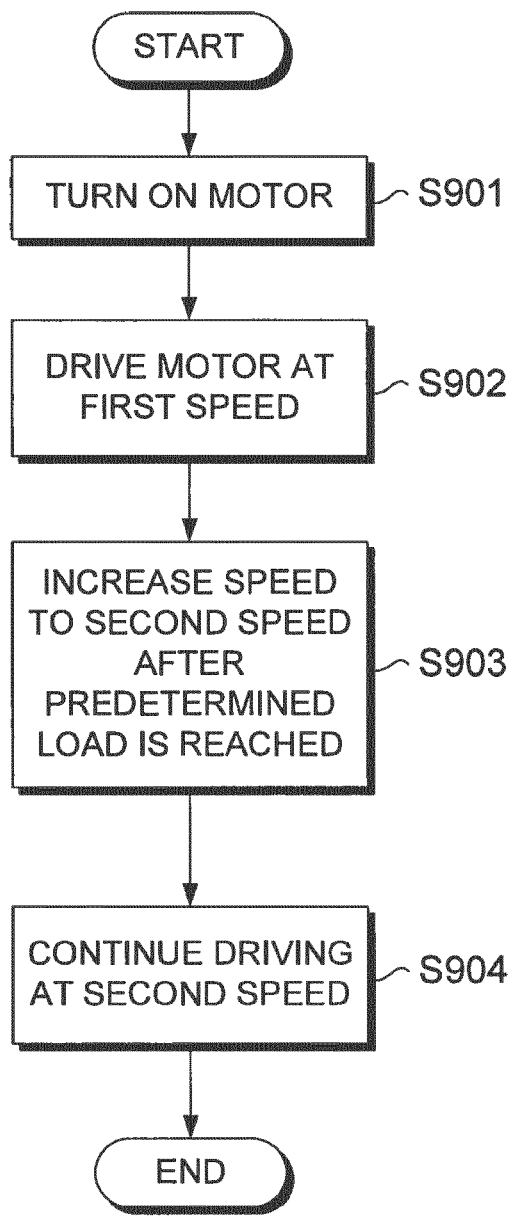
FIG. 9 illustrates a method for use in a breast pump system such as the one shown in FIG. 6.

Referring now to FIG. 9, a method for use in a breast pump system is illustrated. The method can be implemented in any of the breast pump systems described above with reference to FIGS. 1, 2, 4 and 6, or in any conventional breast pump system not including the features of the above-described systems. A motor speed regulating module can be provided to implement the method. In a first step S901, the electric motor is turned on and in step S902 the motor is initially driven at a first speed. Then, in step S903 the motor speed is increased from the first speed to a second speed, higher than the first speed, after a load on the motor reaches a predetermined level. Then, in step S904, the system continues to drive the motor at the second speed.

In step S903, various approaches are possible. In one embodiment, the breast pump system can include a load detecting module arranged to detect a load on the motor, and provide feedback to the motor speed regulating module, which can increase the motor speed after the predetermined load has been reached. Alternatively, instead of providing feedback the system can wait a predetermined time period before driving the motor at the second, higher, speed. The predetermined time period can be determined during calibration of the breast pump system, by measuring a time taken for the load to reach the predetermined level under normal operating conditions. Various ramp profiles can be applied when increasing the motor speed. The speed can be increased gradually as the load increases, from the first speed to the second speed, or can be increased in a step change from the first to the second speed when the predetermined load is reached.

This method is advantageous in a breast pump system, where the load on the motor is low at the beginning of each pumping cycle when there is no vacuum. As air is pumped out of the breast pump funnel to increase the vacuum level, the load on the motor is increased. In a conventional system, when constant power is supplied to the motor throughout the pumping cycle, the motor initially runs at a high speed at the start of the pump cycle as the load is low but the power supplied is relatively high for the low load. This results in excessive noise due to the high initial speed of the motor, which is irritating for a user. In the present embodiment, the motor is purposefully driven at a low speed after being turned on, to reduce the motor noise. The motor can be driven at the low first speed by supplying a low voltage, or by using PWM control and a reduced duty cycle.

A further aspect of the breast pump system will now be described with reference to FIG. 10. The features of this aspect of the breast pump system can be implemented in any of the breast pump systems described above with reference to FIGS. 1, 2, 4 and 6, or in any conventional breast pump system not including the features of the above-described systems.

Figure 10:
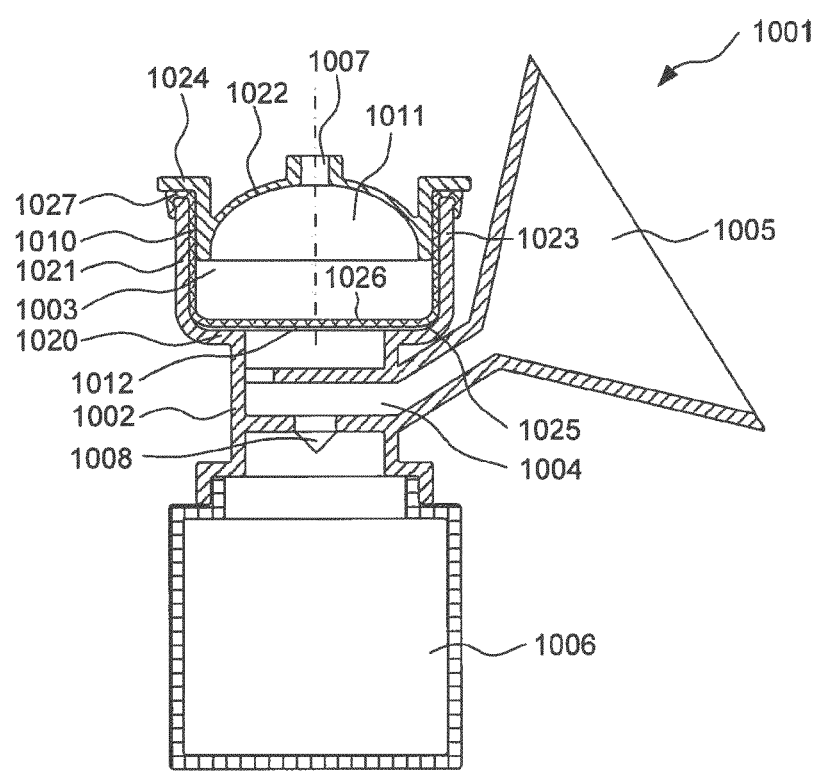
FIG. 10 illustrates a cross-sectional view of the breast pump shown in FIG. 1.

A breast pump 1001 is illustrated in FIG. 10. The breast pump 1001 is similar to the breast pump illustrated in FIG. 1, and is provided for use with in a breast pump system such as that shown in FIG. 1. The breast pump 1001 has a main body 1002 in which a chamber 1003 is defined. The chamber 1003 is formed along a fluid passageway 1004 between a funnel 1005 for receiving a user's breast and a collection vessel 1006. The chamber 1003 has a vacuum port 1007. The vacuum port 1007 communicates with the vacuum pump in an operating unit, similar to the operating unit described in the above embodiments. Therefore, the vacuum pump is able to cause a pressure reduction in the chamber 1003. The vacuum port 1007 is formed at the upper end of the chamber 1003.

A membrane 1010 is received in the chamber 1003. The membrane 1010, also known as a diaphragm, is flexible. The membrane 1010 separates the chamber 1003 into a first space 1011 and a second space 1012. The first space 1011 is in fluid communication with the vacuum port 1007. Therefore, a pressure reduction is generated in the first space 1011 by the vacuum pump. The second space 1012 is in fluid communication with the fluid passageway 1004 between the breast receiving space of the funnel 1005 and the collection vessel 1006. A one-way valve 1008 is disposed in the fluid passageway 1004. The one-way valve 1008 prevents the need to draw air from the collection vessel 1006 to generate a pressure reduction, and also prevents the need to provide a sealed interface between the vessel and the main body 1002.

When a pressure reduction or vacuum is generated in the first space 1011, the membrane 1010 deforms and is drawn in the direction of the first space 1011. Therefore, a pressure reduction is produced in the second space 1012 of the chamber 1003 due to the deformation of the membrane 1010. When a breast is received in the mouth of the funnel, a pressure reduction is formed in the funnel 1005 which acts on the user's breast and urges milk to be expressed therefrom.

The chamber 1003 has a base 1020, a sidewall 1021 and an upper wall 1022. The sidewall 1021 extends between the base 1020 and the upper wall 1022. The sidewall 1021 extends circumferentially around the chamber 1003. The chamber 1003 is formed from lower and upper portions 1023, 1024 which are mountable to each other. The lower portion 1023 defines the base 1020 and a lower part of the sidewall 1021. The upper portion 1024 defines the upper wall 1022 and an upper part of the sidewall 1021. An outer rim of the membrane 1010 is mountable between the upper and lower portions 1023, 1024. Therefore, the membrane 1010 is fixedly mounted in the chamber 1003. This means that the membrane 1010 is held in position in the chamber 1003.

The vacuum port 1007 communicates with the chamber 1003 through the upper wall 1022 and the fluid passageway 1004 communicates with the chamber 1003 through the base 1020. The base 1020, sidewall 1021 and upper wall 1022 define an inner surface of the chamber 1003.

In the present embodiment, the main body 1002 forming the chamber is formed from polypropylene. The flexible membrane 1010 is formed from silicone. However, it will be understood that the chamber 1003 and membrane 1010 may be formed form other suitable materials.

The flexible membrane 1010 has a predefined shape. In the present arrangement, the membrane 1010 has a substantially cup-shaped arrangement in its neutral position, i.e. when it has not been deformed by a reduced pressure in the first space 1011. The membrane 1010 has a lower face 1025 and an upper face 1026. A lip 1027 extends from the free end of a membrane side wall. However, it will be understood that the membrane may be formed to have an alternative shape. With the present arrangement, the lip 1027 is mounted between the lower and upper portions 1023, 1024 forming the cavity 1003. In the present embodiment, the membrane inverts as the membrane 1010 deforms. However, it will be understood that in an alternative embodiment the membrane 1010 does not invert.

The sidewall 1021 has a textured surface. That is, at least a section of the surface of the chamber has a textured surface. In the present embodiment, the lower part of the sidewall 1021 is configured to have a textured surface. The textured surface may extend over all of the surface of the lower part of the sidewall 1021, or only a section of it. The section may comprise the section of the sidewall which will come into contact with the membrane 1010. The textured surface may cover all or part of the chamber surface. For example, there can be a series of repeated patterns extending around the circumference of the chamber each of which have a surface texture.

The textured surface is formed from a textured surface finish having an arithmetical mean roughness (Ra) in the range of Ra 0.8 µm to Ra 3.2 µm. It has been found that a completely smooth, i.e. high gloss finish (±Ra 0.05 µm) can result in a high squeaking noise being caused by the flexible membrane 1010 and the surface of the chamber sticking to each other when the membrane 1010 is deformed in the chamber 1003.

It has also been found that a surface with a high roughness, for example greater than Ra 3.2 µm, may result in higher wear of the membrane 1010 as it moves over the surface. Therefore, a surface finish in the range of Ra 0.8 µm to Ra 3.2 µm will minimise the noise created by the deflection of the membrane 1010 relative to the surface whilst minimising wear of the membrane due to the surface.

In one embodiment, the surface having a textured surface has an arithmetical mean roughness (Ra) of Ra 1.6 µm. It has been determined that a surface with this value of arithmetical mean roughness produces minimal noise during use of the breast pump whilst minimising wear of the membrane.

The textured surface is formed by in-mould texturing. That is, the textured surface is formed by adding a texture to the tool to form the main body 1002, for example a spark erosion texture. Alternatively, the textured surface is formed following production of the main body, for example by sandblasting. Alternative methods of forming the textured surface may be used.

When the breast pump is assembled, the membrane 1010 is received in the chamber 1003. The lower face 1025 of the membrane 1010 is disposed proximate to, but slightly spaced from, the surface of the chamber 1003, for example the lower part of the sidewall 1021. The membrane 1010 is then in its neutral, or undeformed, position. Alternatively, the lower face 1025 of the membrane 1010 may be locate against the surface of the chamber 1003 in its neutral position.

When the breast pump 1001 is operated, a pressure reduction is caused in the first space 1011 and so the membrane 1010 is urged to deform. As the membrane 1010 starts to deform the membrane 1010 is either urged into contact with the surface of the chamber 1003, or is initially in contact with the surface of the chamber 1003. It will be understood that the section of the surface of the chamber 1003 that comes into contact with the membrane 1010 is configured to have a textured surface.

As the membrane 1010 is urged to further deform, the lower face 1025 of the membrane 1010 is drawn away from and/or over the surface of the sidewall 1021 as the membrane 1010 is urged to deform due to a reduction in pressure in the first space 1011 of the chamber 1003. Similarly, it will be understood that the lower face 1025 of the membrane 1010 is moved against and/or over the face of the sidewall 1021 as the membrane 1010 is urged to return to its neutral position due to a release of the reduction in pressure in the first space 1011 of the chamber 1003.

As the membrane 1010 comes into contact with, or moves away from, the textured surface the area of contact formed between the membrane 1010 and the surface of the chamber 1003 is minimised. Therefore, the noise generated due to the membrane 1010 and the surface of the chamber 1003 moving relative to each other is minimised. For example, there is less sticking between the membrane 1010 and the surface of the chamber 1003 due to the reduced surface area.

One advantage of a section of the chamber having a textured surface is that the reduction in surface area contact between the membrane and the surface of the chamber will minimise the friction caused between the membrane and the chamber. Therefore, it will be easier to move the membrane in the chamber. This means that less energy is required to deform the membrane in the chamber and also to return the membrane to its neutral position.

Although in the above embodiment the textured surface is formed on the lower part of the sidewall between the base and the membrane, it will be understood that the textured surface may also, or alternatively, be formed on the upper part of the sidewall between the membrane and the upper wall. This arrangement minimises any noise created through contact between the membrane and the upper part of the sidewall.

Although in the above embodiments the textured surface is formed on the sidewall of the chamber, it will be understood that the textured surface may be formed on any surface of the main body against over which the membrane comes into contact, or moves away from, during deformation of the membrane. In particular, the base and/or the upper wall may also have a textured surface.

Although the textured surface finish is formed on a surface on the chamber in the above described embodiments, it will also be understood that the textured surface may also, or alternatively, formed on the surface of the membrane. This would have the same effect of reducing the contact area between the surface of the membrane and the surface of the chamber. The textured surface may be formed on all or part of the lower face of the membrane, and/or all or part of the upper face of the membrane.

It will be appreciated that although embodiments have been described and illustrated as including certain elements, which may be referred to as components, modules or units, the structures shown are exemplary only. The elements illustrated can be physically separate hardware components, or can be integrated into a single module performing the functionality of the individual modules shown in any of the embodiments. For example, in FIG. 2 the description of a voltage detecting module 224 and motor interrupt module 225 does not imply that these modules are physically separate. In an embodiment, both modules can be embodied in a single chip, including an ADC as the voltage detecting module 224 and additional hardware arranged to perform the function of the motor interrupt module 225. In some embodiments the functions of one or more components may be performed by a processor executing software instructions.

Although in the above described embodiments the pump unit is provided with separate means for generating the pressure reduction in the vacuum path and releasing the pressure reduction in the vacuum path, it will be understood that they may be integrated. In another embodiment, the pump unit comprises a piston slidably received in a piston chamber or cylinder. The piston acts as a reciprocating element. The piston forms a fluid seal in the chamber. The piston chamber forms part of the vacuum path. The piston is reciprocally operated, for example, by a crankshaft and a motor. When the piston is drawn along the piston chamber, the movement of the piston acts to generate a pressure reduction in the vacuum path. Therefore, a vacuum may be produced at the user's breast. When the piston moves in the opposite on its return stroke the pressure reduction in the chamber is released. However, in the event that the piston becomes stuck or the motor fails, for example, then the piston will not release the pressure reduction in the vacuum path. That is, the pump unit will fail to release the pressure reduction in the vacuum path. If this occurs, then the leakage aperture provided in the vacuum path will allow a controlled release of the pressure reduction in the vacuum path.

In the above embodiment, it will be understood that the vacuum path is formed between the piston and a user's breast when the breast pump system is assembled and a user's breast is received in the funnel. The pump unit may be disposed in the operating unit or may be housed in the breast pump.

In another embodiment, the pump unit is formed by the membrane and a means of mechanically deforming the membrane. The membrane acts as a reciprocating element. For example, a rod may be attached to the deformable membrane which is movable in a reciprocal manner by an electric motor. With such an arrangement the deformation of the membrane from its neutral condition generates a pressure reduction in the vacuum path. Subsequently, the return of the membrane to its neutral condition releases the pressure reduction in the vacuum path. In this embodiment it will be understood that the vacuum path is formed between the membrane and a user's breast when the breast pump system is assembled and a user's breast is received in the funnel. However, in the event that the membrane does not return to its neutral condition, for example due to failure of the electric motor, then the membrane will not release the pressure reduction in the vacuum path. That is, the pump unit will fail to release the pressure reduction in the vacuum path. If this occurs, then the leakage aperture provided in the vacuum path will allow a controlled release of the pressure reduction in the vacuum path. The membrane may be the membrane described in the above embodiments or may be another membrane disposed separately.

In the above two embodiments, it will be understood that no pressure release valve is required because the reduction in pressure is released by the valve or membrane returning to its neutral position.

It will also be appreciated that the term "comprising" does not exclude other elements or steps and that the indefinite article "a" or "an" does not exclude a plurality. A single processor may fulfil the functions of several items recited in the claims. The mere fact that certain measures are recited in mutually different dependent claims does not indicate that a combination of these measures cannot be used to an advantage. Any reference signs in the claims should not be construed as limiting the scope of the claims.

Although claims have been formulated in this application to particular combinations of features, it should be understood that the scope of the disclosure of the present invention also includes any novel features or any novel combinations of features disclosed herein either explicitly or implicitly or any generalisation thereof, whether or not it relates to the same invention as presently claimed in any claim and whether or not it mitigates any or all of the same technical problems as does the parent invention. The applicants hereby give notice that new claims may be formulated to such features and/or combinations of features during the prosecution of the present application or of any further application derived therefrom.

The invention claimed is:

1. A breast pump system comprising:
   a pump unit;
   an actuator for driving the pump unit; and
   a power supply arranged to supply electrical power to the actuator; characterized by
   an actuator speed regulating module arranged to drive the actuator at a first speed when the pump unit is turned on, and to continue to drive the actuator at a second speed higher than the first speed after a load on the actuator reaches a predetermined level.

2. The breast pump system according to claim 1, wherein the power supply is arranged to supply the electrical power to the actuator using pulse width modulation PWM, and is arranged to supply the first voltage by supplying the electrical power with a first duty cycle and to supply the second voltage by supplying the electrical power with a second duty cycle higher than the first duty cycle.

3. The breast pump system according to claim 1, wherein the power supply is arranged to gradually increase the first voltage up to the second voltage during the predetermined time period.

4. The breast pump system according to claim 1, further comprising:
   a power supply control module arranged to detect an input current supplied to the actuator and reduce the speed of the actuator in response to the detected input current exceeding a threshold current level indicative of a threshold vacuum level at a breast pump.

5. The breast pump system according to claim 4, wherein the power supply control module is arranged to suspend the supply of electrical power to the actuator in order to reduce the speed of the actuator.

6. The breast pump system according to claim 4, wherein the pump unit further comprises:
   a vacuum pump, and
   a valve for releasing a vacuum generated by the vacuum pump,
   wherein in response to the detected input current exceeding the threshold current level, the power supply control module is further arranged to indicate a failure of the valve.

7. The breast pump system according to claim 4, wherein the power supply is arranged to supply the electrical power to the actuator using pulse width modulation PWM according to a duty cycle, and the power supply control module is arranged to suspend the supply of electrical power to the actuator by setting the PWM duty cycle to substantially zero.

8. The breast pump system according to claim 1, further comprising:
   a power supply control module arranged to control the power supply to supply a first voltage to the actuator when the pump unit is turned on and to supply a second voltage, higher than the first voltage, to the actuator after a predetermined time period after the actuator is turned on.

9. The breast pump according to claim 8, wherein the second predetermined time period is a time taken for a pressure difference generated by the pump unit to reach a predetermined level.

10. A breast pump system according to claim 1, further comprising:
    a breast pump having
    a chamber, and
    a membrane receivable in the chamber to separate the chamber into first and second spaces,
    wherein the membrane is deformable in the chamber in response to a reduction of pressure in the first space to cause a reduction of pressure in the second space, and
    a surface of the chamber contactable with the membrane, and/or a surface of the membrane contactable with the chamber, has a textured surface finish so that the noise level generated as the membrane comes into contact with, moves along, or moves away from, the chamber is minimised.

11. A breast pump system according to claim 10, wherein the chamber comprises a sidewall against which the membrane locates prior to and/or during deformation, the surface having the textured surface finish being formed by the sidewall and/or the section of membrane contactable with the sidewall.

12. A breast pump system according to claim 10, wherein the surface has a textured surface finish with an arithmetical mean roughness (Ra) between Ra 0.4 µm and Ra 3.2 µm.

13. A method for use in a breast pump system comprising a pump unit, a actuator for driving the pump unit, and a power supply arranged to supply electrical power to the actuator, the method being characterized by:
    driving the actuator at a first speed when the pump unit is turned on; and
    continuing to drive the actuator at a second speed higher than the first speed after a load on the actuator reaches a predetermined level.

14. The method of claim 13, further comprising:
    detecting an input current supplied to the actuator; and
    reducing the speed of the actuator in response to the detected input current exceeding a threshold current level indicative of a threshold vacuum level at a breast pump.

15. The method of claim 13, further comprising:
    supplying the electrical power by supplying a first voltage to the actuator when the pump unit is turned on; and
    supplying a second voltage, higher than the first voltage, to the actuator after a predetermined time period after the actuator is turned on.

* * * * *